United States Patent [19]

Schick

[11] Patent Number: 5,587,108
[45] Date of Patent: Dec. 24, 1996

[54] STYRENE MONOMER BASED NAIL TIP BLENDER AND BRUSH CLEANER

[75] Inventor: Michael R. Schick, Nashotah, Wis.

[73] Assignee: European Touch Co., Inc., Milwaukee, Wis.

[21] Appl. No.: 319,278

[22] Filed: Oct. 6, 1994

[51] Int. Cl.$^6$ .............. C08K 5/01; C08K 5/07; C08K 5/15; A61K 7/04
[52] U.S. Cl. .............. 252/364; 106/311; 424/61
[58] Field of Search ............ 252/364; 106/311; 424/61

[56] References Cited

U.S. PATENT DOCUMENTS

| | | | |
|---|---|---|---|
| 3,552,401 | 1/1971 | Michaelson | 132/73 |
| 4,425,326 | 1/1984 | Guillon et al. | 424/61 |
| 4,649,045 | 3/1987 | Gaske et al. | 424/61 |
| 4,766,005 | 8/1988 | Montgomery et al. | 427/4 |
| 4,804,486 | 2/1989 | Day | 252/153 |
| 4,837,057 | 6/1989 | Bartoszek-Loza et al. | 524/831 |
| 4,863,993 | 9/1989 | Montgomery | 524/854 |
| 4,943,530 | 7/1990 | Christner et al. | 435/188 |
| 5,108,751 | 4/1992 | Hagan et al. | 424/401 |
| 5,206,011 | 4/1993 | Pappas et al. | 424/61 |
| 5,275,807 | 1/1994 | Pappas et al. | 424/61 |

OTHER PUBLICATIONS

ARCO Chemical Company, "Styrene Monomer" (11 pages).
Chevron Chemical Company, "Safe Handling & Storage of Styrene Monomer" (22 pages).
Du Pont, "Permeation Guide for Du Pont Protective Apparel Fabrics", Oct. 1992, (8 pages) H–42422.
"Chemical Resistance Table and Material Selection Guide", (pp. 11–15).
Ansell Edmont Industrial, "Ansell Edmont Chemical Resistance Guide", 1990, (8 pages) 5th Edition Form No. CRG-–GC-REV.990.
Cole–Parmer Instrument Company, "Chemical resistance charts", (pp. 1043–1050).
ARCO Chemical Company, "Material Safety Data Sheet on Gamma Butyrolactone", Nov. 2, 1990, (7 pages).

*Primary Examiner*—Robert E. Sellers
*Attorney, Agent, or Firm*—Nilles & Nilles, S.C.

[57] ABSTRACT

A quick drying nail tip blender and brush cleaner for use in beauty salons for the purpose of smoothly blending an edge of a synthetic nail to the surface of a natural nail comprises styrene monomer, acetone, gamma butyrolactone, flagrance and safflower oil. The compound avoids the sue of conventional chlorinated solvents.

10 Claims, 1 Drawing Sheet

STYRENE MONOMER BASED NAIL TIP BLENDER AND BRUSH CLEANER

BACKGROUND OF THE INVENTION

1.0 Field of the Invention

The present invention relates generally to solvents for nail tip blending and brush cleaning. More particularly, the present invention relates to a solvent for nail tip blending and brush cleaning comprised of a styrene monomer base and gamma butyrolactone and acetone additives.

2.0 Background and Related Art

A variety of methods and compositions for beautifying nails, particularly human fingernails, are well known. One such method involves attaching a synthetic nail to a human nail. For example, U.S. Pat. No. 3,552,401 issued to Michaelson, et al. discloses a solvent-permeable, supple and conformable synthetic nail structure which is differentially responsive to solvent and shaped for invisible securement to a human nail.

A main problem that is encountered when utilizing synthetic nails is illustrated in FIG. 1. A synthetic fingernail 14 beautifies a natural fingernail 10 by elongating it past a natural fingernail edge 16. However, relying as it does on thickness and stiffness, the synthetic nail 14 leaves a distinct edge 12 at its termination line. This may be temporarily satisfactory where a full synthetic nail is applied, but with time the normal growth of the natural fingernail carries this unsightly edge outward across the natural nail surface. Hence, a method of nail tip blending is needed to eliminate this unsightly edge, and thereby blend the synthetic nail with the natural nail surface.

Michaelson '401 discloses one method of overcoming this problem. The Michaelson synthetic nail structure is differentially responsive to solvent (as already mentioned), and the edge portion can be locally solubilized (possibly to the point of complete disintegration) by applying an appropriate solvent.

Conventional solvents used for such nail blending purposes frequently comprise high percentages of chlorinated fluorocarbons, chlorinated acetone, and other chlorinated solvents. However, due to the high tendency of liquid chlorine to pass into a vapor state, using chlorinated solvents in high percentages as a nail tip solvent and beauty aid is undesirable. Inhalation of a chlorinated solvent in high concentrations is toxic and narcotic, and in reduced concentrations is at least toxic. Some chlorinated solvents, in particular chlorinated fluorocarbons, have also been associated with depletion of atmospheric ozone. The volatility of chlorinated solvents is an especially serious problem in beauty parlors, where manicurists are chronically exposed to solvent vapors in the course of their daily work activities.

One compound which has reduced volatility is styrene monomer. The nail care industry has rarely recognized the possibility of using styrene monomer in a nail care products generally, and has not recognized at all the possibility of using styrene monomer in nail blending solvents. For example, see U.S. Pat. No. 5,275,807 and U.S. Pat. No. 5,206,011 issued to Pappas, et at.; U.S. Pat. No. 4,766,005 issued to Montgomery, et al.; and U.S. Pat. No. 4,425,326 issued to Guillon, et al. All four of these patents disclose using acetone in nail care products, but none of them disclose using styrene monomer (and none of them relate to nail blending solvents). The possibility of using styrene monomer in a nail care product has not gone completely unnoticed, however. For example, U.S. Pat. No. 4,649,045 issued to Gaske, et al. discloses preferably using styrene monomer in a thermoplastic coating composition to be used as a nail polish. Gaske, et al. do not disclose, however, that styrene monomer could be used in a nail blending solution.

In addition to the concern about workplace health hazards, another concern is the fact that the brush used to apply the solvent should be cleaned after each use. Typically, this is accomplished by mounting the brush to the cap of the solvent container, such that when the cap is replaced the brush soaks in the solvent solution. Hence, it is highly desirable that the solvent solution be effective as a brush cleaner.

SUMMARY OF THE INVENTION

A main objective of this invention is to provide an alternative solvent solution from traditional chlorinated solvents which can partially dissolve an edge of a synthetic nail and which is also effective as a brush cleaner. In accordance with this objective, a styrene monomer based nail tip blender and brush cleaner which includes gamma butyrolactone and acetone additives is presented. A solvent of the present invention comprises about 20% to about 50% by weight of styrene monomer; about 20% to about 60% by weight of acetone; about 15% to about 30% by weight of gamma butyrolactone; and about 1% to about 10% by weight of a mixture comprising safflower oil and fragrance.

A second main objective of this invention is to provide a method of attaching a synthetic nail to a natural nail. A method of the present invention comprises the steps of attaching the synthetic nail to the natural nail with an adhesive; applying a catalyst for instantly drying the adhesive and adhering the synthetic nail to the natural nail; and applying a solvent comprising about 20% to about 50% by weight of styrene monomer, about 20% to about 60% by weight of acetone, and about 15% to about 30% by weight of gamma butyrolactone to the synthetic nail, in order to partially dissolve the synthetic nail and thereby blend the upper surface of the synthetic nail to the upper surface of the natural nail.

Other objects, features, and advantages of the present invention will become apparent to those skilled in the art from the following detailed description and accompanying drawings. It should be understood, however, that the detailed description and specific examples, while indicating preferred embodiments of the present invention, are given by way of illustration and not of limitation. Many changes and modifications within the scope of the present invention may be made without departing from the spirit thereof, and the invention includes all such modifications.

DETAILED DESCRIPTION OF THE PREFERRED EMBODIMENT

Figure 1:
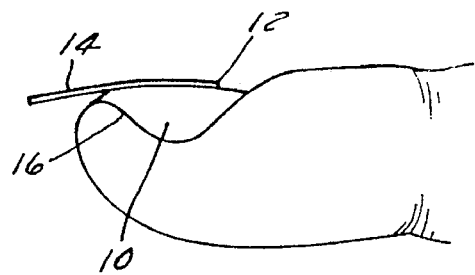
FIG. 1 is a side view of synthetic fingernail attached to a natural fingernail, wherein there is a distinct edge at the termination line of the synthetic fingernail.
Figure 2:
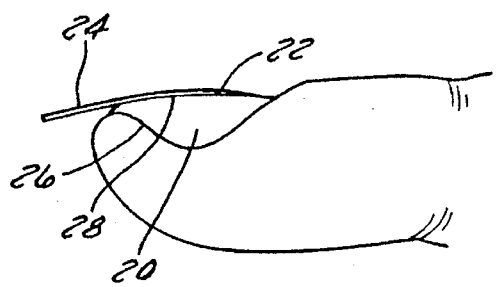
FIG. 2 is a side view of synthetic fingernail attached to a natural fingernail, wherein the present invention has been used to blend the synthetic fingernail with the natural fingernail so that there is no distinct edge and a termination line is not visible.

Referring now to FIG. 2, a side view of a synthetic fingernail 24 attached to a natural fingernail 20 is illustrated. A synthetic nail is typically made from nylon or ABS plastics. The synthetic fingernail 24 beautifies the natural fingernail 20 by elongating it past a natural fingernail edge 26. Actual testing of the solvent of the present invention has demonstrated that, when applied to the synthetic fingernail 24, the solvent partially dissolves an edge 22 of the synthetic fingernail 24. As a result, the synthetic fingernail 24 is naturally blended to the natural fingernail 20 so that there is no distinct edge and a termination line is not visible.

The solvent of the present invention comprises, inter alia, styrene monomer. Through testing, it has been found that the invention works well when it comprises about 20% to about 50% by weight of styrene monomer. The invention works even better when the amount of styrene monomer is kept within the range of about 25% to about 45% by weight, and better still if kept within the range of about 30% to about 40%. In the preferred embodiment, the invention comprises about 36% by weight of styrene monomer.

The solvent of the present invention also comprises acetone. Through testing, it has been found that the invention works well when it comprises about 20% to about 60% by weight of acetone. The invention works even better when the amount of acetone is kept within the range of about 30% to about 50% by weight, and better still if kept within the range of about 35% to about 45%. In the preferred embodiment, the invention comprises about 40% by weight of styrene monomer.

The solvent of the present invention further comprises gamma butyrolactone. Through testing, it has been found that the invention works well when it comprises about 15% to about 30% by weight of gamma butyrolactone. The invention works even better when the amount of gamma butyrolactone is kept within the range of about 15% to about 25% by weight. In the preferred embodiment, the invention comprises about 20% by weight of gamma butyrolactone.

Finally, the solvent of the present invention comprises a mixture comprising safflower oil and fragrance. Through testing, it has been found that the invention works well when it comprises about 1% to about 10% by weight of this mixture. The invention works even better when the amount of this mixture is kept within the range of about 3% to about 7% by weight. In the preferred embodiment, the invention comprises about 4% by weight of this mixture. Of that mixture, the majority is fragrance, about 3.9%.

As compared to conventional nail blending solvents, the solvent of the present invention avoids the use of chlorinated solvents and instead uses styrene monomer. Using styrene monomer avoids the disadvantages that have been recently associated with the use of chlorinated solvents. Two key factors in evaluating the hazards that a compound, and more specifically a nail blending solvent, presents are (1) the evaporation rate of the compound and (2) the toxicity of the evaporated vapors. The first factor is important because there will be no hazardous vapors to be breathed from a compound that does not evaporate. Hence, a reduced evaporation rate corresponds to a reduced mount of vapors in the air.

The second factor, the toxicity of the evaporated vapors, is of obvious importance. The amount of compound required to produce negative health results varies widely from compound to compound. As a guide in the control of health hazards, the Occupational Safety and Heath Administration (OSHA) assigns a threshold limit value (TLV) to airborne substances in workroom air. Threshold limit values are time weighted averages based on conditions which it is believed that workers may be repeatedly exposed to day after day without adverse effects. A lower TLV denotes a more toxic vapor.

When the health hazards of acetone and styrene monomer are evaluated based on these two factors, styrene monomer is found to be more safe because of its lower evaporation rate (volatility). In regards to the first factor, the evaporation rate of a given compound is based on its vapor pressure and varies with temperature. The vapor pressure of acetone is 184.0 mm Hg, whereas the vapor pressure of styrene monomer is only 6.5 mm Hg. Hence, the evaporation rate of styrene monomer is dramatically slower than the evaporation rate of acetone (although the exact values will vary with temperature). In regards to the second factor, styrene monomer does have a lower TLV value than acetone (50 ppm in air for styrene monomer as compared to 750 ppm in air for acetone) and is therefore more hazardous when evaluated based on the second factor alone. When both factors are considered together, however, styrene monomer is found to be less hazardous overall.

Figure 3:
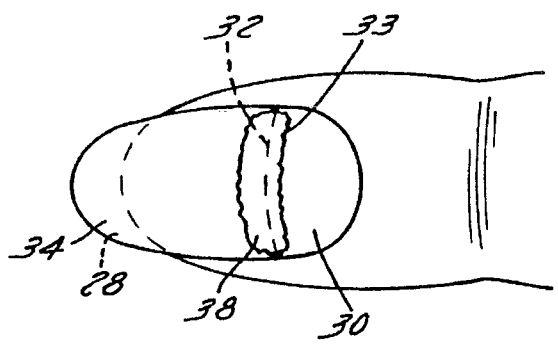
FIG. 3 is a top view of synthetic fingernail attached to a natural fingernail, wherein the solvent of the present invention has been applied to the synthetic fingernail.

Referring now to FIG. 3, a top view of a synthetic fingernail 34 attached to a natural fingernail 30 is illustrated. The preferred method of attaching the synthetic fingernail 34 to the natural fingernail 30 comprises two steps. First, the synthetic fingernail 34 is attached to the natural fingernail 30. An adhesive may be applied to the lower (or inner) surface 28 of the synthetic nail, and the synthetic nail then presses onto the upper surface of the natural nail. Further, a catalyst may be applied for quick drying of the adhesive and thereby instantly bonding the synthetic nail to the natural nail.

Second, a solvent 38 is applied which comprises about 36% by weight of styrene monomer, about 40% by weight of acetone, about 20% by weight of gamma butyrolactone, and about 4% by weight of a mixture of fragrance and safflower oil to the synthetic fingernail 34, thereby partially dissolving the synthetic fingernail 34. As illustrated, the solvent 38 is applied in the general region 33 around the distinct edge 32. When applied, the solvent 38 partially dissolves the edge 32 and makes it no longer visible. As a result, the synthetic fingernail 34 is naturally blended to the natural fingernail 30 to provide a smooth transitional surface region 33 from the upper surface of the synthetic nail to the upper surface of the natural nail.

Figure 4:
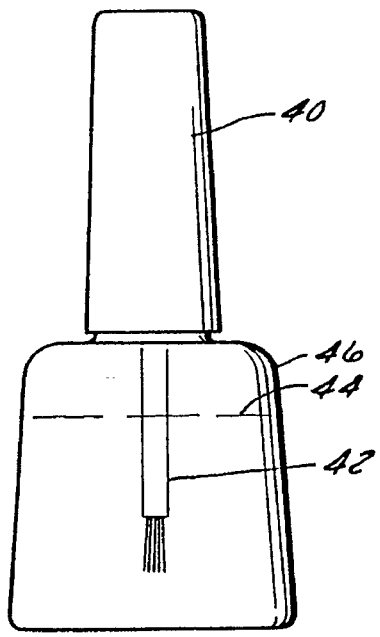
FIG. 4 is a side view of a bottle which contains the solvent of the present invention, wherein an applicator brush is soaking in the solvent and is simultaneously being cleaned.

Referring now to FIG. 4, a side view of a bottle 46 which contains solvent 44 of the present invention is illustrated. FIG. 4 demonstrates why it is highly desirable that a nail blending solvent be effective as a brush cleaner as well. An applicator brush 42 is mounted to a cap 40, and is soaking in the solvent 44. Because the solvent 44 is an effective brush cleaner, the brush 42 is cleaned as it soaks in the solvent 44.

The base chemicals are available from a number of commercial suppliers. For instance, styrene monomer is available from ARCO Chemical Company, Newtown Square, Penna. and from Chevron Chemical Company, Houston, Tex. Gamma buryrolactone is also available from ARCO, and acetone and safflower oil is widely available. The fragrance used in this compound should be of a type used for making the odor of styrene monomer and is likewise normally available from the chemical supplier.

The embodiments described herein are given by way of illustration and not of limitation. Many changes and modifications within the scope of the present invention may be made without departing from the spirit thereof. For example, the invention could also be used where synthetic nail structures are used on human toenails or on the nails of animals. It is to be understood that the embodiments of the present invention not disclosed herein are fully intended to be within the scope of the appended claims.

We claim:

1. A solvent for partially dissolving an edge of a synthetic nail, said solvent comprising:

A) about 20% to about 50% by weight of styrene monomer;
   B) about 20% to about 60% by weight of acetone;
   C) about 15% to about 30% by weight of gamma butyrolactone; and
   D) about 1% to about 10% by weight of a mixture comprising safflower oil and fragrance.

2. The solvent as in claim 1, wherein said styrene monomer is included in an amount ranging from about 25% to about 45% by weight.

3. The solvent as in claim 2, whereto said acetone is included in an mount ranging from about 30% to about 50% by weight.

4. The solvent as in claim 3, wherein said gamma butyrolactone is included in an amount ranging from about 15% to about 25% by weight.

5. The solvent as in claim 4, wherein said mixture comprising safflower oil and fragrance is included in an amount ranging from about 2% to about 8% by weight.

6. The solvent as in claim 1, wherein said styrene monomer is included in an amount ranging from about 30% to about 40% by weight.

7. The solvent as in claim 6, wherein said acetone is included in an amount ranging from about 35% to about 45% by weight.

8. The solvent as in claim 7, wherein said gamma butyrolactone is included in an amount ranging from about 18% to about 22% by weight.

9. The solvent as in claim 8, wherein said mixture comprising safflower oil and fragrance is included in an amount ranging from about 3% to about 7% by weight.

10. A solvent for partially dissolving an edge of a synthetic nail, said solvent comprising:

A) about 36% by weight of styrene monomer;
   B) about 40% by weight of acetone;
   c) about 20% by weight of gamma butyrolactone; and
   D) about 4% by weight of a mixture comprising safflower oil and fragrance.

* * * * *